United States Patent [19]

Hobbs

[11] 4,448,894

[45] May 15, 1984

[54] CATALYST AND REVERSE DISPROPORTIONATION PROCESS

[75] Inventor: Charles F. Hobbs, Des Peres, Mo.

[73] Assignee: Monsanto Company, St. Louis, Mo.

[21] Appl. No.: 514,724

[22] Filed: Jul. 18, 1983

Related U.S. Application Data

[62] Division of Ser. No. 403,254, Jul. 29, 1982, Pat. No. 4,419,526.

[51] Int. Cl.³ .............................................. B01J 23/31
[52] U.S. Cl. .................... 502/249; 502/246; 502/250; 502/306; 502/311; 502/243; 502/353; 585/435; 585/646
[58] Field of Search ............... 502/120, 243, 246, 248, 502/249, 250, 353, 306, 311; 585/435, 438, 646

[56] References Cited

U.S. PATENT DOCUMENTS

| | | | |
|---|---|---|---|
| 3,658,930 | 4/1972 | Kenton et al. | 260/683 D |
| 3,728,414 | 4/1973 | Van Helden et al. | 260/683 D |
| 3,764,635 | 10/1973 | Fattore et al. | 260/683 D |
| 3,792,107 | 2/1974 | Fattore et al. | 260/683 D |
| 3,965,206 | 6/1976 | Montgomery et al. | 260/669 R |
| 4,144,197 | 3/1979 | Riesser et al. | 252/462 |
| 4,192,961 | 3/1980 | Polyakov et al. | 585/319 |
| 4,300,007 | 11/1981 | Polyakov et al. | 585/323 |

FOREIGN PATENT DOCUMENTS 1205677  9/1970  United Kingdom .

Primary Examiner—Delbert E. Gantz
Assistant Examiner—Anthony McFarlane

[57] ABSTRACT

A catalyst containing tungsten, antimony and an alkali or alkaline earth component on a support, preferably silica gel, is disclosed which is useful in reverse disproportionation of stilbene and ethylene to produce styrene.

7 Claims, No Drawings

CATALYST AND REVERSE DISPROPORTIONATION PROCESS

This is a division of application Ser. No. 403,254, filed July 29, 1982 now U.S. Pat. No. 4,419,526.

BACKGROUND OF THE INVENTION

1. Field of the Invention

The present invention relates to a catalyst and process for reverse disproportionation of ethylene and stilbene to produce styrene. The catalyst comprises tungsten, antimony and an alkali or alkaline earth component on a support, preferably silica gel.

2. Description of the Prior Art

The production of styrene from stilbene and ethylene is disclosed in U.S. Pat. No. 3,965,206, the teachings of which are incorporated by reference. Use of conventional disproportionation catalysts such as cobalt molybdate on alumina, or tungsten oxide or silica, alumina or silica-alumina, for reverse disproportionation is taught.

U.S. Pat. No. 3,764,635, Fattore, et al, the teachings of which are incorporated by reference, teaches a process for disproportionating olefins using a catalyst of tungsten and bismuth on a support, preferably silica. The catalyst is active for disproportionation without any activation step.

U.S. Pat. No. 3,792,107, Fattore, et al, the teachings of which are incorporated by reference, discloses use of a catalyst of tungsten and copper or tungsten and Group VIII metals, preferably Fe, Co or Ni, on silica or other support. It is claimed that this catalyst requires no activation before use in disproportionation.

U.S. Pat. No.3,728,414, Helden, et al, the teachings of which are incorporated by reference, teaches a conventional olefin disproportionation catalyst with a promoter, a Group IIIa metal on an alumina carrier. Conventional olefin disproportionation catalysts are said to contain titanium, vanadium, chromium, manganese, zirconium, niobium, molybdenum, technetium, ruthenium, rhodium, palladium, tin, hafnium, tantalum, tungsten, rhenium, osmium, and iridium. This reference teaches that additional components, e.g., coactivators, hydrogenating components, components for isomerization of the double bond, and the like may also be added. Coactivators listed include cobalt oxide, and compounds of iron, nickel, and bismuth.

U.S. Pat. No. 4,192,961 teaches conversion of a mixture of dibenzyl and stilbene with ethylene in the presence of a catalyst of chromium oxide, tungsten oxide, an oxide of an alkali metal and silica or alumisilicate. Styrene yields of 78 to 80 wt %, based upon conversion of ethylbenzene, dibenzyl and stilbene, are claimed.

U.S. Pat. No. 3,658,930, Kenton, et al, the teachings of which are incorporated by reference, teaches disproportionation of olefins using a rhodium oxide promoter on conventional olefin disproportionation catalyst, e.g., tungsten, molybdenum, rhenium, or tellurium on silica.

U.K. Patent Specification No. 1,205,677 teaches disproportionation of olefins using a conventional catalyst, such as molybdenum trioxide, tungsten trioxide or rhenium heptoxide on alumina, silica, or alumina-silica and incorporating into this conventional catalyst a second component to effect double bond isomerization of olefins. Group VIII noble metals are suggested as being suitable, with preferred isomerization catalysts containing platinum and especially palladium. An alkali or alkaline earth metal ions are added to the catalyst to serve as a base to inhibit the oligomerization of branch chained olefins.

None of these prior art catalysts are believed to possess sufficient activity and stability to permit their use in a commercial reverse disproportionation process.

Another failing of most prior art catalysts is that a relatively high temperature activation procedure is necessary before the catalysts are suitable for use. These catalysts are extremely active, but have very short lives before carbon and coke deposition destroys catalytic activity. Frequent regeneration and activation of the catalyst are necessary for a successful commercial process. It is desirable to minimize stress on the catalyst, and on the equipment by eliminating large temperature swings necessary for activation and regeneration of the catalyst. It is also desirable if the catalyst has great stability, and is able to operate for relatively long periods.

SUMMARY OF THE INVENTION

The present invention provides a catalyst comprising catalytically-effective amounts of antimony, tungsten and an alkali or alkaline earth component on a carrier material.

In another embodiment, the present invention provides a process for the reverse disproportionation of stilbene and ethylene which comprises contacting stilbene and ethylene at reverse disproportionation conditions with an activated catalyst containing catalytically-effective amounts of antimony, tungsten, and an alkali or alkaline earth component or compounds thereof supported on a carrier material to produce styrene.

In a more limited embodiment, the present invention provides a process for the reverse disproportionation of stilbene and ethylene into styrene comprising contacting the stilbene and ethylene at a temperature of 300 to 600 C. with an activated catalyst comprising tungsten, antimony, and an alkali or alkaline earth metal component or compound thereof on silica gel carrier, and wherein the atomic ratio of antimony to tungsten is from 1:20 to 1:1, to produce styrene, and continuing said contact until said catalyst has been at least partially deactivated by coke deposition, removing said deactivated catalyst from contact with reactants and regenerating said catalyst by oxidizing coke from said catalyst with an oxygen containing gas to produce an oxidized catalyst with reduced coke content and thereafter activating said catalyst by contacting said oxidized catalyst with activating gas at 400 to 600 C. for a time sufficient to activate said catalyst, and thereafter returning said catalyst to contact with stilbene and ethylene for further reverse disproportionation of stilbene and ethylene into styrene.

DETAILED DESCRIPTION

The Reverse Disporportionation Reaction

The total reaction of this invention may be represented by the following equation:

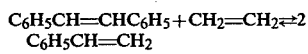

Catalyst

The catalyst may contain from 0.1 to 10 wt % W, preferably 1 to 6 wt %, and 0.003 to 4 wt % Sb, preferably 0.1 to 1.5 wt %. The catalyst also has 0.01 to 2%, preferably 0.03 to 0.2 wt % alkali or alkaline earth metal ion, preferably potassium. Other promoters may be present.

The support is preferably silica gel, but any other support used for conventional disproportionation catalysts may also be used though the catalyst performance may change some.

Activation

Activation is necessary to achieve the catalyst's full potential. Activation is a partial reduction of the catalytic components, which are oxides because of the calcination step used in catalyst manufacture, or because of the oxidizing atmosphere used to burn off coke on spent catalyst. Conventional activation procedures, such as used for conventional disproportionation catalysts may be used.

Reaction Conditions

The reverse disproportionation reaction conditions are given in U.S. Pat. No. 3,965,206, the teachings of which are incorporated by reference. In general, temperatures of 300 to 600 C. are adequate. Pressures from subatmospheric to 1000 atm, absolute are suitable, but operation at 1 to 10 atmospheres gives good results.

Hydrogen or nitrogen or inerts may be present during the disproportionation reaction. Adding hydrogen may or may not cut down on catalyst coking, but may overreduce the catalyst. Nitrogen, and hydrogen and other inert gases, will also cut down residence time of reactants in the reactors, if desired. I prefer to operate with reactants as the sole feed to the reactor.

The feed to the process of the present invention consists of relatively pure stilbene and ethylene. Other materials may be present, but polar materials act as catalyst poisons.

EXAMPLES

Reactor

The experimental apparatus used in all examples consisted of a 0.5-inch OD stainless steel tube, 18–31 cm long. The catalyst was maintained in the reactor as a fixed bed. Reactants flowed in a vapor phase, down flow, through the catalyst bed. The catalyst was supported on a quartz wool plug resting on an inert support. During the early phases of the study, $\frac{1}{8}$-inch alundum beads were used, but experiments showed that this material was not inert and caused some coking. The later studies were conducted using $\frac{1}{8}$-inch long, quartz billets cut from 2 mm rod as a support.

Special precautions were taken to exclude oxygen from the apparatus and to keep the stilbene feed in the vapor phase. Special steam tracing, heating, and nitrogen purging of lines contacting stilbene are essential in a pilot plant, but may not be as critical in a large scale commercial plant.

Catalyst Preparation

A series of catalysts was prepared. The basic catalyst contained 0.56 wt % $WO_3$ and 0.038 wt % $K_2O$. The catalyst was prepared by adding 20 g of 14–35 mesh Davison Grade 59 silica gel, which had been freshly calcined, to 28 ml of a solution containing 5 ml of 0.0236 N KOAc solution, 10 ml of $H_2O$, and 13 ml of concentrated $NH_4OH$. The silica gel was only minimally wetted by the 28 ml of liquid. The mixture was shaken for 30 minutes, then dried overnight in a stream of air on a filter, and finally calcined for 2 hours at 600 C. Various additives, those which were soluble in the alkaline solution described above, were simply added to the alkaline solution along with the potassium and tungsten components. In some cases, because of solubility limitations, ammonium hydroxide would not dissolve the additive, so in these cases a few drops of concentrated $HNO_3$ was added to obtain a clear solution. In all cases the total liquid volume of impregnating solution was 28 ml, the exact volume was obtained by adjusting the amount of water added. In all cases, except where noted, additives were added sufficient to give an atomic ratio of tungsten:additive of 5:1. I believe the additives, the added metallic components, were present as oxides on the catalysts, because of the calcination in air for two hours at 600 C.

When rhodium was added, a different procedure was used as no water soluble rhodium compound was readily available. A large batch of base catalyst (containing 0.56 wt % $WO_3$ and 0.038 wt % $K_2O$) was made up as described above. A 20.12 g portion of this catalyst was then impregnated with 25 ml of a methanol solution containing 0.0375 g of Rh (acac). This alcoholic impregnating solution was sufficient to just impart wetness to the catalyst. After shaking for 30 minutes, drying in air, and calcining for 2 hours at 600 C. the catalysts were ready for use.

Table I shows a listing of catalysts prepared.

TABLE I

| Additive | Compound Used | Wt. of Compound[a], g. | Comments |
|---|---|---|---|
| Pt | $Pt(NH_3)_2(ONO)_2$ | 0.0330[b] | |
| Pd | $Pd(NH_3)_2(ONO)_2$ | 0.0232 | 5 drops $HNO_3$, boiled to dissolve salts |
| Ni | $Ni(NO_3)_3.6H_2O$ | 0.0281 | No $NH_4OH$ |
| Zn | $Zn(OAc)_2.2H_2O$ | 0.0212 | No $NH_4OH$; 5 drops 30% $H_2O_2$ |
| Cr | $Cr(NO_3)_3.9H_2O$ | 0.0387 | No $NH_4OH$; 5 drops 30% $H_2O_2$ |
| Fe | $Fe(NO_3)_3.9H_2O$ | 0.0390 | No $NH_4OH$; 5 drops 30% $H_2O_2$; 10 drops $HNO_3$ |
| Ru | $RuNO(NO_3)_3$ | 0.0306[c] | 5 drops 30% $H_2O_2$ |
| Mo | $(NH_4)_6Mo_7O_{24}.4H_2O$ | 0.0171 | |
| V | $NH_4VO_3$ | 0.0114[d] | |
| Sn | $SnSO_4$ | 0.0218 | No $NH_4OH$; 10 drops conc. $H_2SO_4$, 4 drops $HNO_3$ |
| Re | $Re_2O_7.3$ (Dioxane) | 0.0362 | No $NH_4OH$; 5 drops 30% $H_2O_2$ |
| Ag | $AgNO_3$ | 0.0164 | |
| Ce | $Ce(NO_3)_3.6H_2O$ | 0.0419 | No $NH_4OH$ |
| Eu | $Eu(NO_3)_3.6H_2O$ | 0.0431 | No $NH_4OH$ |
| As | $As_2O_5.nH_2O$ | 0.0127[e] | No $Nh_4OH$ |
| U | $UO_2)C_2H_3O_2)_2.2H_2O$ | 0.0410 | No $NH_4OH$ |
| Mn | $Mn(C_2H_3O_2).4H_2O$ | 0.0237 | No $NH_4OH$ |
| Rh | Rh(acac) | 0.0375 | Alcoholic impregnation |
| Sb | $Sb_2H_2C_8H_4O_{12}.3H_2O$[f] | 0.0323 | Only 2.05 ml of KOAc, No $NH_4OH$ |

TABLE I-continued

| Additive | Compound Used | Wt. of Compound[a], g. | Comments |
|---|---|---|---|
|  |  | 0.0326 |  |

[a] 20 g of silica gel base
[b] 61.00% Pt
[c] 35.87% Ru
[d] 76.90% $V_2O_5$
[e] 87.65% $As_2O_5$
[f] tartrate

Catalyst Activation

Catalysts were activated, in situ, by passing 200 scc/min of 60 CO over the catalyst at a specified temperature for specified time. It is possible to use other activating gases, or no gas at all, but a CO activation procedure was chosen as a standard one to permit screening of the effects of various additives on catalyst activation.

Test Procedure

The activated catalyst was then tested for its activity on a standard feed consisting of 200 scc/min ethylene and 40 scc/min of stilbene. The residence time in the catalyst bed was 0.3 seconds. The products were analyzed by gas chromatography.

After the catalyst lost activity, it was regenerated by contacting it with 48 scc/min of air for 45 minutes at 575 C.

A typical operating sequence is presented below:

A. Activation Cycle
1. 25 min. Nitrogen purge of lines and reactor system (200 cc/min). Ethylene purge of line up to oxygen trap. Reactor temperature equilibrated to activation temperature.
2. 5 min. Nitrogen purge continuing. Ethylene purge of lines through oxygen trap to vent, located at ethylene-to-saturator feed valve. CO flow to vent to purge CO line in panel control board.
3. 55 min., typical. Nitrogen off. CO feed to reactor for activation, feed rate typically 200 cc/min. Ethylene purge to vent continuing, with oxygen meter (Teledyne Trace Oxygen Analyzer Model 311-1) connected to vent to monitor ethylene quality.
4. 5 min. Nitrogen purge to vent to clear lines in control panel. CO feed to reactor and ethylene feed to vent continuing.
5. 15 min. Nitrogen purge of reactor and lines. Ethylene feed to vent continuing. Temperature change to disproportionation run temperature.
6. 5 min. Ethylene feed to reactor, by-passing saturator. Saturator feed valve open to reactor to equalize pressure.

B. Disproportionation Cycle
1. 30 min. Ethylene feed through stilbene saturator and thence to reactor; GC sampling program called during last 60 sec. of cycle. Step is repeated as desired.

C. Burn-off Cycle
1. 5 min. Nitrogen purged to vent to clear lines in control panel. Ethylene feed to saturator off, but saturator feed valve to reactor open to equalize pressure.
2. 60 min. Nitrogen purge to reactor (48 cc/min). Temperature changed to burn-off temperature, usually 575 C. Air purged to vent to equilibrate pressure in line.
3. 45 min. Air feed to reactor, 48 cc/min. GC analysis for $CO_2$ called.
4. 15 min. Nitrogen purge, 200 cc/min, through reactor system.
5. Shut down or recycle.

This procedure was used to test the different catalyst formulations. Experimental results are shown as productivity, measured as moles of styrene per liter of catalyst per hour. 34 moles per liter per hour represents about 83% conversion of stilbene to styrene. Productivity is reported both for the start of run conditions (initial) and at the end of the run, i.e., after 4.5 hours of operation (final). The data are presented below in Table IIA.

TABLE IIA

EFFECT OF ADDITIVES ON CATALYST ACTIVATION

| Catalyst[a] Additive | Activation Conditions | | Productivity[b] | |
|---|---|---|---|---|
|  | Time | Temp. | Initial | Final |
| None (STD) |  | None | 4.19 | 6.74 |
|  | 1 hr | 450 | 8.05 | 12.65 |
|  | 8 hr | 450 | 27.65 | 19.43 |
| Ce | 1 hr | 450 | 8.13 | 12.30 |
| Eu |  | None | 4.01 | 6.27 |
|  | 1 hr | 450 | 6.91 | 12.57 |
| As |  | None | 2.16 | 3.99 |
|  | 1 hr | 450 | 8.62 | 12.91 |
|  | 1 hr | 450 | 8.92 | 13.31 |
| Fe | 1 hr | 450 | 9.07 | 17.79 |
| Cr | 1 hr | 450 | 7.10 | 12.20 |
| Ni | 1 hr | 450 | 7.51 | 13.82 |
| Ru | 1 hr | 450 | 4.68 | 11.19 |
| Pt | 1 hr | 450 | 9.38[c] | 7.21[c] |
| Pd | 1 hr | 450 | 7.29[c] | 6.35[c] |

[a] All additives at 5:1 W:additive mole ratio unless otherwise noted.
[b] All runs were for 4.5 hr. Run temp., 425 C.
[c] Average for 2 runs.

The test apparatus was then partially dismantled and rebuilt. A number of additional tests were then run. The main difference between operations reported in Table IIA and Table IIB, presented hereafter, is the amount of oxygen contamination. I believe that the data presented in IIA reflect less oxygen contamination than those in Table IIB. Since the testing occurred under superatmospheric pressure, about 3 psig or 1.2 atm, absolute, it was thought that there could be no air contamination due to leaks in the piping. Reactants might leak out, but air would not get in. Several ppm oxygen diffused into the test apparatus through a leak to increase the oxygen level, and decrease the catalyst activity. Oxygen is a catalyst poison. The amount of $O_2$ contamination was relatively constant during the IIA testing period, I estimate about 0.2 ppm $O_2$ by volume. For the IIB testing period about 0.3 ppm $O_2$ by volume was present. I checked the activity of my standard, or reference, catalyst periodically during the IIA and IIB testing periods. The standard, or reference, catalyst consistently gave lower productivity during the IIB tests. The results of the more O₂ contaminated runs are reported in Table IIB.

TABLE IIB
EFFECT OF ADDITIVES ON CATALYST ACTIVATION

| Catalyst<sup>a</sup> Additive | Activation Conditions | | Productivity | |
|---|---|---|---|---|
| | Time | Temp. | Initial | Final |
| None (STD) | 1 hr | 450 | 6.09 | 11.04 |
| | 1 hr | 450 | 5.87 | 11.49 |
| | 1 hr | 450 | 4.53 | 9.63 |
| Rh | 1 hr | 450 | 9.82 | 10.60 |
| | 1 hr | 450 | 2.98 | 8.16 |
| | 1 hr | 450 | 2.41 | 7.45 |
| | 8 hr | 450 | 2.76 | 6.53 |
| Mo | 1 hr | 450 | 3.92 | 7.75 |
| | 1 hr | 450 | 4.75 | 7.56 |
| V | 1 hr | 450 | 1.05 | 2.86 |
| Sn | 1 hr | 450 | 0.04 | (0.18) |
| | 1 hr | 450 | 1.34 | (1.61) |
| Re | 1 hr | 450 | 4.49 | 4.26 |
| Zn | 1 hr | 450 | 2.82 | 4.32 |
| Ag | 1 hr | 450 | 3.42 | 8.02 |
| | 1 hr | 450 | 4.32 | 8.48 |
| U | 1 hr | 450 | 4.98 | 5.47 |
| Mn | 1 hr | 450 | 3.76 | 4.04 |
| Sb | 1 hr | 450 | 10.07 | 9.28 |

<sup>a</sup>All additives at 5:1 W:additive mole ratio unless otherwise noted.

It is believed that results can be compared very well within Table IIA, or within Table IIB. Direct comparison of an additive listed in Table IIB with an additive from the Table IIA is harder to make, because of the increased oxygen contamination in those runs presented in Table IIB. It is believed that the relative activities, i.e., activity of a catalyst in Table IIB with an additive compared to activity of a catalyst with no additives from Table IIB can be compared. These data relative activation, for initial activity, are reported in Table III. The relative initial activities are probably more significant than relative end of run activities, so comparisons were made based on relative initial activities.

TABLE III

| Additive | Relative Activities |
|---|---|
| Sb | 2.08 |
| Fe | 1.13 |
| As | 1.10 |
| Pt | 1.09 |
| Ce | 1.01 |
| Rh | 1.10, 0.56, 0.45 |
| U | 1.03 |
| None (Standard) | 1.00 |
| Re | 0.93 |
| Ag | 0.89, 0.71 |
| Mo | 0.89, 0.74 |
| Ni | 0.93, 0.77 |
| Cr | 0.88 |
| Eu | 0.86 |
| Pd | 0.85 |
| Mn | 0.78 |
| Zn | 0.58 |
| Ru | 0.58 |
| Sn | 0.31 |
| V | 0.16, 0.17, 0.20, 0.20 |

Repeated tests showing declining activities meant that a catalyst could not be regenerated, but lost some activity with each cycle. A single number, e.g., Sb's relative activity of 2.08 meant that essentially all activity was restored after coke burn-off, and activation. The Rh catalyst lost activity after coke burn-off and activation.

From these data, it is apparent that a reverse disproportionation catalyst of tungsten and potassium containing relatively small amounts of antimony gives excellent results. Activation is necessary to achieve full productivity possessed by this catalyst.

I know a one-to-five ratio of antimony: tungsten gives good results. I believe that good results can be obtained with Sb:W atom ratios of 1:20 to 2:1 and preferably 1:10 to 1:3. The effects of Sb are not nearly as pronounced when a more severe activation step is used. A series of tests with 575 C. activation for 1 hour gave Sb:W:K catalysts with about 10% greater initial productivity, but about 25% less final productivity as compared to a W:K catalyst.

If I were designing a commercial plant today, I would conduct further experiments to see if the various catalytic components could be optimized further. I would probably use a catalyst containing 2 to 10 times as much metal content as those catalysts used in the experiments. Commercially, you want more active catalysts, and smaller reaction vessels, and would use catalysts with a higher metal loading. I used very lightly loaded catalysts for my experiments because the catalyst was extremely active. "Full strength" catalyst established equilibrium conditions so rapidly that I could not discern relatively smaller differences caused by different additives. Based on other experimental work, metal loadings ten times as high can probably be achieved using similar impregnation procedures, with five or tenfold increase in activity. Phrased another way, the reactants see the active metals, not the support, and the amount of conversion per gram of catalytic components (excluding support) is roughly constant. More metal on the support should improve the catalyst resistance to trace amounts of O₂ and polars.

I would like to learn more about the active form of the catalysts I tested. The active form may be a simple oxide or may be a mixed heteropolyacid of $SiO_2$, $WO_3$ and $MO_x$, where M is the additive metal. It is possible that the oxides mentioned and claimed do not exist as discrete oxides, but instead form some complex polymeric structure.

I would operate a commercial plant with whatever oxygen stripping columns or oxygen and water absorbers were necessary to ensure oxygen, and other contaminants, especially polar ones, were excluded from the plant.

My catalyst can be disposed within the reactor as a fixed bed, fluidized bed, moving bed, ebullated bed, or any other reactor configuration. The advantage of the fluidized, moving and ebullating bed reactors is that catalyst addition and withdrawal can be performed continuously. Thus, coke, or carbon deposition on the catalyst can be burned off, the catalyst activated, and returned to the reactor without shutting down the reactor. The disadvantage of this mode of operation is that the reactor designs are fairly complicated, as compared to simple fixed bed, down flow design. When fixed bed reactors are used, preferably, two or three reactors are provided in parallel, permitting one or more reactors to be taken off stream for carbon burn-off and activation while the other reactor(s) remain on stream.

What is claimed is:

1. A catalyst comprising catalytically-effective amounts of antimony, tungsten and an alkali or alkaline earth component on a carrier material.

2. Catalyst of claim 1 wherein the carrier material is silica gel.

3. Catalyst of claim 1 wherein the alkali or alkaline earth component is potassium.

4. Catalyst of claim 1 wherein the catalyst contains 0.1 to 10 wt % W, 0.01 to 2 wt % alkali or alkaline earth component and 0.03 to 4 wt % Sb, and the carrier material is silica gel.

5. Catalyst of claim 1 wherein the catalyst contains 1 to 6 wt % W as $WO_3$, 0.1 to 1.5 wt % Sb as $Sb_2O_3$, and 0.03 to 0.2 wt % K as $K_2O$, and the carrier material is silica gel.

6. Catalyst of claim 1 wherein the Sb:W atomic ratio is 1:20 to 2:1.

7. Catalyst of claim 1 wherein the Sb:W atomic ratio is 1:5.

* * * * *